United States Patent
Weismann et al.

(10) Patent No.: US 6,260,550 B1
(45) Date of Patent: Jul. 17, 2001

(54) DEVICE AND PROCESS FOR CONTROLLING A RESPIRATOR

(75) Inventors: Dieter Weismann, Gross Grönau; Michael Rehfeldt, Lübeck, both of (DE)

(73) Assignee: Dräger Medizintechnik GmbH (DE)

(*) Notice: Subject to any disclaimer, the term of this patent is extended or adjusted under 35 U.S.C. 154(b) by 0 days.

(21) Appl. No.: 09/399,721

(22) Filed: Sep. 20, 1999

(30) Foreign Application Priority Data

Nov. 4, 1998 (DE) .............................................. 198 50 770

(51) Int. Cl.[7] ........................................................ A62B 9/02
(52) U.S. Cl. .................................. 128/205.24; 128/203.25
(58) Field of Search ............................. 128/914, 205.19, 128/203.25, 204.24, 204.25, 204.26, 205.24

(56) References Cited

U.S. PATENT DOCUMENTS

| | | | | |
|---|---|---|---|---|
| 1,214,941 | * | 2/1917 | Morris et al. | 128/204.25 |
| 2,547,458 | * | 4/1951 | Goodner | 128/204.25 |
| 2,581,450 | * | 1/1952 | Seeler | 128/204.25 |
| 3,859,995 | * | 1/1975 | Colston | 128/204.25 |
| 4,112,938 | * | 9/1978 | Jeretin | 128/204.23 |
| 4,448,192 | * | 5/1984 | Stawitcke et al. | 128/204.26 |
| 5,400,778 | * | 3/1995 | Jonson et al. | 128/205.19 |
| 5,615,699 | * | 4/1997 | Olsson et al. | 128/203.25 |
| 5,797,393 | * | 8/1998 | Kohl | 128/204.23 |
| 5,810,002 | * | 9/1998 | Dittmann | 128/203.25 |
| 5,957,130 | * | 9/1999 | Krahbichler et al. | 128/205.19 |
| 6,106,480 | | 8/2000 | Gama De Abreu et al. | 600/529 |

FOREIGN PATENT DOCUMENTS

| | | |
|---|---|---|
| 25 07 981 B2 | 3/1977 | (DE) . |
| 195 16 536 A1 | 11/1996 | (DE) . |
| WO 98/12963 | 4/1998 | (WO) . |

* cited by examiner

*Primary Examiner*—Aaron J. Lewis
(74) *Attorney, Agent, or Firm*—McGlew and Tuttle, P.C.

(57) ABSTRACT

A respirator with an inhalation line (5) connected to a gas supply device (2) and with an exhalation line (7) connected to an exhalation device (3), with a Y piece (8) connecting the inhalation line (5) to the exhalation line (7), and with a patient connection (9) going out from the Y piece (8). Partial rebreathing of $CO_2$-containing exhaled air is made possible in a simple manner by providing a switchover device (4) between the inhalation line (5) and the gas supply device (2) as well as between the exhalation line (7) and the exhalation device (3). The switchover device is designed such that the flow connection is established between the inhalation line (5) and the gas supply device (2) as well as the exhalation line (7) and the exhalation device (3) in a first switching position and there is at least a flow connection between the gas supply device (2) and the exhalation line (7) in the second switching position.

6 Claims, 1 Drawing Sheet

DEVICE AND PROCESS FOR CONTROLLING A RESPIRATOR

FIELD OF THE INVENTION

The present invention pertains to a respirator device with an inhalation line connected to a gas supply device and with an exhalation line connected to an exhalation device, with a Y piece connecting the inhalation line to the exhalation line and with a patient connection going out from the Y piece. The present invention also pertains to a process for controlling a respirator, which has a switchover device between a gas supply device and an inhalation line as well as an exhalation line and an exhalation device.

BACKGROUND OF THE INVENTION

A respirator of this type has become known from DE 195 16 536 A1. The prior-art respirator is used for pressure- and volume-controlled forms of respiration, the breathing strokes being triggered either by a timing control or by the patient's spontaneous breathing activity. It is often necessary in respiration therapy and respiration diagnostics to raise the $CO_2$ level in the blood in order to thereby stimulate the breathing. The enrichment of the $CO_2$ may be achieved, e.g., by the partial rebreathing of the previously exhaled gas. The pulmonary blood flow can be determined in a noninvasive manner by specific $CO_2$ rebreathing.

The $CO_2$ content in the inhaled air can be influenced by an additional volume connected into the breathing gas line in the vicinity of the patient, by which the dead space in the breathing gas line is increased. Such a device for increasing the dead space has been known from DE 25 07 981. The drawback of the prior-art dead space increase is that it must be arranged in the vicinity of the patient connection and cannot be used for routine applications because of its relatively large volume. Since the respiration is usually performed with breathing gas enriched with water vapor up to the saturation, a large amount of condensate is produced in the dead space volume, and this condensate must be disposed of continuously.

In the device known from WO 98/12963, the line section between the Y piece and the patient connection is split into two lines, between which switchover is possible by means of a 3/2-way valve, one of the lines having a larger dead space for rebreathing than the other line. This device also has the drawback that the additional dead space volume is located in the vicinity of the patient connection with the handling and condensation problems associated therewith.

SUMMARY AND OBJECTS OF THE INVENTION

The basic object of the present invention is to improve a respirator of the type such that a partial rebreathing of $CO_2$-containing exhaled air is made possible in a simple manner and to provide a process for controlling the respirator.

According to the invention, a respirator is provided with an inhalation line connected to a gas supply device and with an exhalation line connected to an exhalation device. A Y piece connects the inhalation line to the exhalation line. A patient connection goes out from the Y piece. A switchover device is provided such that the flow connection between the inhalation line and the gas supply device as well as the exhalation line and the exhalation device is established in a first switching position and that there is at least a flow connection between the gas supply and the exhalation line in a second switching position. The switchover device is provided between the inhalation line and the gas supply device as well as between the exhalation line and the exhalation device, wherein the gas flow through the inhalation line is interrupted in the second switching position.

The process according to the present invention for controlling the respirator includes providing a switchover device between a gas supply device and an inhalation line as well as an exhalation line and a exhalation device. The switchover device is operated in a first mode of operation such that there is a flow connection between the inhalation line and the gas supply as well as the exhalation line and the exhalation device. The switchover device is operated in a second mode of operation such that the exhalation line is connected to the gas supply device, while the gas flow in the inhalation line is interrupted in the second mode of operation.

The advantage of the present invention is essentially that a switchover device, by which the breathing gas flow can be deflected during the breathing-in period into the exhalation line, is provided between the inhalation line, the exhalation line and the respirator, so that the patient will also breathe in part of the $CO_2$-containing breathing gas previously exhaled, besides fresh breathing gas. The extent of the enrichment with $CO_2$ is obtained from the volume enclosed by the exhalation line. This volume may be changed by selecting certain tube lengths and tube diameters as well as by an additional volume.

The switchover device may be arranged as a separate component between the respirator and the breathing lines. However, it is particularly advantageous for the switchover device to be directly integrated in the respirator. Thus, no change recognizable for the user from the outside is made on the connections of the device for the exhalation line and the inhalation line. By deflecting the inhalation gas into the exhalation line and utilizing the gas volume present in the exhalation line at the same time for the next inhalation stroke, no additional components are needed for increasing the dead space in the vicinity of the patient.

It is especially advantageous to operate the switchover device such that the second switching position, in which the gas supply device is connected to the exhalation line, is switched on during a certain time interval of the inhalation period only. The volume of the rebreathed gas and consequently the inhaled $CO_2$ concentration can thus be varied. For the rest of the inhalation phase, the switchover device is in the first switching position, in which the gas supply device is connected to the inhalation line.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
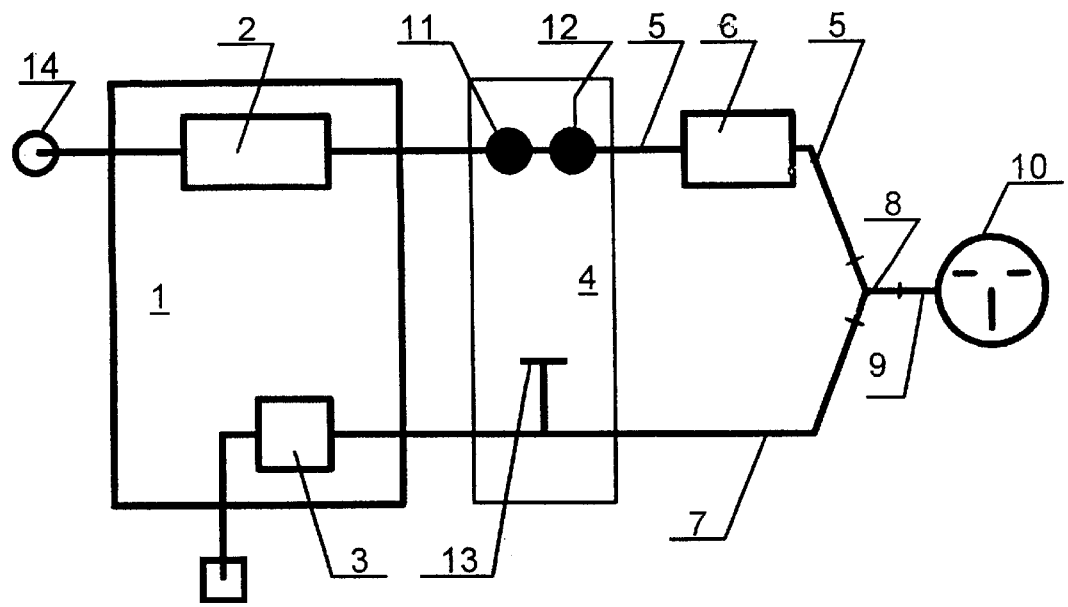
FIG. 1 is a schematic diagram of a respirator with a switchover device, which is in a switching position without $CO_2$ enrichment.

Referring to the drawings in particular, FIG. 1 schematically shows a respirator 1 with a gas supply device 2 and an exhalation device 3, with a switchover device 4 connected to the gas supply device 2 and to the exhalation device 3, with an inhalation line 5 with a humidifier 6 and with an exhalation line 7, wherein the inhalation line 5 and the exhalation line 7 are connected to a patient connection 9 via a Y piece 8. In a first switching position of the switchover device 4 shown in FIG. 1, the inhalation line 5 is connected to the gas supply device 2 and the exhalation line 7 is connected to the exhalation device 3. A patient 10 located at the patient connection 9 breathes in inhalation gas via the inhalation line 5 and the humidifier 6 from the gas supply device 2 connected to a gas source 14, and the exhalation takes place via the exhalation line 7 and the exhalation device 3. The switchover device 4 has valve openings 11, 12 in the line section between the gas supply device 2 and the inhalation line 5, while a valve opening 13 is located in the line section between the exhalation device 3 and the exhalation line 7. In the first switching position of the switchover device 4 shown in FIG. 1, the valve openings 11, 12 are connected to one another, while the valve opening 13 is closed.

Figure 2:
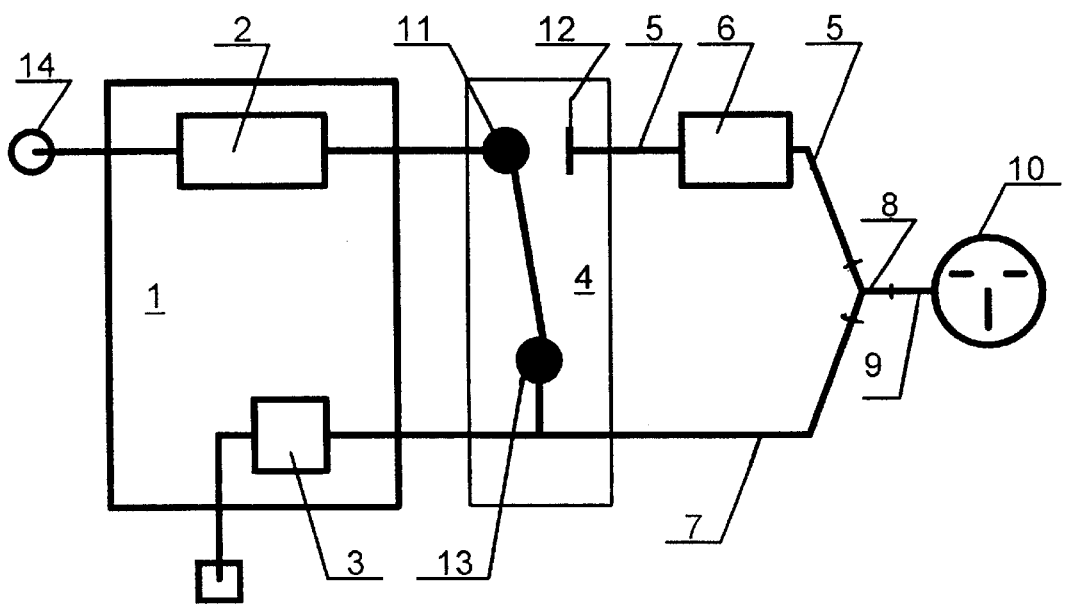
FIG. 2 is a schematic diagram of the respirator according to FIG. 1 with a switching position of the switchover device for $CO_2$ enrichment.

FIG. 2 shows a second switching position of the switchover device 4, in which part of the gas previously exhaled is inhaled again during the next inhalation stroke. To achieve this, the valve openings 11, 13 are connected to one another at the beginning of a new inhalation stroke, so that the breathing gas being supplied by the gas supply device 2 reaches the patient 10 via the exhalation tube 7, the Y piece 8 and the patient connection 9. The valve opening 12 is closed in the second switching position of the switchover device 4.

The breathing gas flows during the phase of exhalation over the exhalation line 7 to the exhalation device 3. If the next inhalation stroke shall be performed without rebreathing of exhaled gas, the switchover device 4 is switched back into the first switching position, FIG. 1.

The volume of the rebreathed gas can be influenced by varying the on time of the second switching position. If, e.g., the second switching position is switched on only during part of the inhalation interval, the rebreathed volume inhaled decreases correspondingly. The maximum attainable rebreathing volume is present if the second switching position is present during the entire inhalation interval.

While a specific embodiment of the invention has been shown and described in detail to illustrate the application of the principles of the invention, it will be understood that the invention may be embodied otherwise without departing from such principles.

What is claimed is:

1. A respirator, comprising:
   a gas supply device;
   an inhalation line connected to said gas supply device;
   an exhalation device;
   an exhalation line connected to said exhalation device;
   a Y piece connecting said inhalation line to said exhalation line;
   a patient connection going out from said Y piece;
   a switchover device having a flow connection between said inhalation line and said gas supply device as well as a flow connection between said exhalation line and said exhalation device in a first switching position, and having at least a flow connection between said gas supply device and said exhalation line in a second switching position, said switchover device being positioned between said inhalation line and said gas supply device as well as being positioned between said exhalation line and said exhalation device, wherein a gas flow through said inhalation line is interrupted in second switching position.

2. The respirator in accordance with claim 1, wherein said switchover device is operated such that the second switching position is present at least during a time interval of an inhalation period.

3. A process for controlling a respirator, the process comprising the steps of:
   providing a switchover device between a gas supply device and an inhalation line as well as between an exhalation line and an exhalation device;
   operating the switchover device in a first mode of operation such that there is a flow connection between the inhalation line and the gas supply device as well as a flow connection between the exhalation line and the exhalation device; and
   operating the switchover device in a second mode of operation such that the exhalation line is connected to the gas supply device while the gas flow in the inhalation line is interrupted in the second mode of operation.

4. The process in accordance with claim 3, wherein said second mode of operation is switched on during a predetermined period of the inhalation phase.

5. A respirator, comprising:
   a Y piece with a first branch, with a second branch and with a third branch;
   a patient connection connected directly to said first branch of said Y piece, said patient connection carrying gas from the Y piece to the patient and from the patient to the Y piece;
   a gas supply device;
   an inhalation line connected to said gas supply device and connected directly to said second branch of said Y piece, said inhalation line carrying gas in the direction of said Y piece from said gas supply device;
   an exhalation valve;
   an exhalation line connected to said exhalation valve and connected directly to said third branch of said Y piece; and
   a switchover device provided between said inhalation line and said gas supply device as well as between said exhalation line and said exhalation valve, said switchover device being switchable into a first switching position providing a flow connection between said inhalation line and said gas supply device and providing a flow connection between said exhalation line and said exhalation valve, and said switchover device being switchable into a second position providing a flow connection between said gas supply device and said exhalation line wherein gas flow through said inhalation line is interrupted and gas flows through said exhalation line in the direction of said Y piece from said gas supply device.

6. The respirator in accordance with claim 5, wherein said switchover device is operated such that the second switching position is present at least during a time interval of an inhalation period.

* * * * *